(12) United States Patent
Bruno et al.

(10) Patent No.: US 12,161,404 B2
(45) Date of Patent: Dec. 10, 2024

(54) LASER ABLATING DEVICE AND METHODS FOR OPERATING AND MANUFACTURING SUCH A DEVICE

(71) Applicant: ADVANCED OSTEOTOMY TOOLS—AOT AG, Basel (CH)

(72) Inventors: Alfredo E. Bruno, Biel-Benken (CH); Michael Peyer, Bern (CH)

(73) Assignee: ADVANCED OSTEOTOMY TOOLS—AOT AG, Basel (CH)

( * ) Notice: Subject to any disclaimer, the term of this patent is extended or adjusted under 35 U.S.C. 154(b) by 711 days.

(21) Appl. No.: 16/472,691

(22) PCT Filed: Dec. 22, 2017

(86) PCT No.: PCT/EP2017/084322
§ 371 (c)(1),
(2) Date: Jun. 21, 2019

(87) PCT Pub. No.: WO2018/115410
PCT Pub. Date: Jun. 28, 2018

(65) Prior Publication Data
US 2019/0365467 A1    Dec. 5, 2019

(30) Foreign Application Priority Data
Dec. 22, 2016   (EP) .................................. 16206432

(51) Int. Cl.
*A61B 18/20*   (2006.01)
*A61B 18/00*   (2006.01)

(52) U.S. Cl.
CPC .... *A61B 18/20* (2013.01); *A61B 2018/00565* (2013.01); *A61B 2018/00577* (2013.01);
(Continued)

(58) Field of Classification Search
CPC .......... A61B 18/20; A61B 2018/00565; A61B 2018/00577; A61B 2018/00601;
(Continued)

(56) References Cited

U.S. PATENT DOCUMENTS

2004/0151217 A1*  8/2004  Yeik ..................... B23K 26/034
                                                      372/69
2010/0292680 A1* 11/2010  Bragagna ............... A61B 18/20
                                                      606/13
(Continued)

FOREIGN PATENT DOCUMENTS

EP       2 119 408 A1    11/2009
JP       2002113017 A     4/2002
(Continued)

OTHER PUBLICATIONS

International Search Report and Written Opinion issued Apr. 4, 2018 in corresponding International Patent Application No. PCT/EP2017/084322.
(Continued)

*Primary Examiner* — John R Downey
(74) *Attorney, Agent, or Firm* — MEDLER FERRO WOODHOUSE & MILLS PLLC

(57) ABSTRACT

A laser ablating device for cutting human or animal natural or artificial hard tissue includes: a cutting laser source adapted to provide a pulsed cutting laser beam lasing at a wavelength suitable for ablating the hard tissue; an imaging laser source adapted to provide an imaging laser beam covering a broadband spectral region; and a beam mixing structure and a movable scanner mirror positioned after the beam mixing structure. The beam mixing structure is adapted to redirect the cutting laser beam of the cutting laser source and/or the imaging laser beam of the imaging laser source such that an optical axis of the cutting laser beam is parallel to an optical axis of the imaging laser beam. The
(Continued)

scanner mirror is arranged to direct the imaging laser beam and the cutting laser beam when having parallel optical axes.

22 Claims, 3 Drawing Sheets

(52) U.S. Cl.
CPC ............... *A61B 2018/00601* (2013.01); *A61B 2018/00642* (2013.01); *A61B 2018/00702* (2013.01); *A61B 2018/00982* (2013.01); *A61B 2018/2025* (2013.01); *A61B 2018/20359* (2017.05)

(58) Field of Classification Search
CPC .......... A61B 2018/00642; A61B 2018/00702; A61B 2018/00982; A61B 2018/2025; A61B 2018/20359
USPC ....................................................... 606/2–19
See application file for complete search history.

(56) References Cited

U.S. PATENT DOCUMENTS

| | | | | |
|---|---|---|---|---|
| 2012/0138586 | A1* | 6/2012 | Webster | B23K 26/20 219/121.64 |
| 2014/0135747 | A1* | 5/2014 | Donitzky | A61B 34/20 606/4 |
| 2015/0327930 | A1* | 11/2015 | Bruno | A61B 18/203 606/11 |
| 2015/0335477 | A1* | 11/2015 | Schuele | A61F 9/00825 606/6 |
| 2016/0135890 | A1* | 5/2016 | Cattin | A61B 18/203 606/11 |
| 2016/0135891 | A1 | 5/2016 | Feldman et al. | |
| 2016/0137544 | A1* | 5/2016 | Jing | B23K 26/146 65/161 |
| 2016/0270848 | A1 | 9/2016 | Varghese et al. | |
| 2019/0175274 | A1* | 6/2019 | Hendrick | A61B 1/00006 |

FOREIGN PATENT DOCUMENTS

| | | |
|---|---|---|
| JP | 2014150889 A | 8/2014 |
| JP | 2016521147 A | 7/2016 |
| WO | 99/55218 A1 | 11/1999 |
| WO | 2009/052866 A1 | 4/2009 |
| WO | 2011/035792 A1 | 3/2011 |
| WO | 2011/091283 A1 | 7/2011 |
| WO | 2012/037694 A2 | 3/2012 |
| WO | 2015/179187 A1 | 11/2015 |
| WO | 2016040791 A1 | 3/2016 |
| WO | 2016/054217 A1 | 4/2016 |

OTHER PUBLICATIONS

Search Report issued Oct. 8, 2021, in Japanese Patent Appl. No. 2019-534294.

* cited by examiner

LASER ABLATING DEVICE AND METHODS FOR OPERATING AND MANUFACTURING SUCH A DEVICE

TECHNICAL FIELD

The present invention relates to a laser ablating device according to the preamble of independent claim 1 and more particularly to a method of operating such a laser ablating device, methods of manufacturing and operating such a laser ablating device and a method of cutting human or animal natural or artificial hard tissue.

Such a laser ablating device comprising a cutting laser source adapted to provide a pulsed cutting laser beam lasing at a wavelength suitable for ablating hard tissue, and an imaging laser source adapted to provide an imaging laser beam covering a broadband spectral region, can be used for cutting human or animal natural or artificial hard tissue such as bones.

BACKGROUND ART

For cutting and drilling materials in various technical fields it has become increasingly popular to use apparatuses which apply a laser beam to the material. Today, in industrial applications such cutting or drilling is widespread since it allows for efficiently and flexibly process work pieces at high precision. Also, for cutting human or animal hard tissue such as bones, cartilages or the like cutting and drilling with laser is more and more applied. For example, in computer assisted surgery it is known to use laser beams as cutting instruments. More particularly, e.g., in WO 2011/035792 A1 a computer assisted and robot guided laser osteotomic medical device is described which allows for precise and gentle drilling and cutting of bone and other human or animal hard and also soft tissue.

A common problem in known laser induced photoablation of human or animal hard tissue relates to controlling cutting depth, beam intensity and repetition rate in pulsed lasers. In contrast to laser induced photoablation widely used in micromachining of non-biological materials such as metals and plastics, issues with respect to collateral damages are of crucial importance when photoablating human or animal hard tissue. Such collateral damages can occur, e.g. as carbonization, due to heating caused by inappropriate laser beam intensities, e.g., into neighboring soft tissue. Or, they can also occur due to photoablation beyond the depth of the targeted hard tissue. Making these problems even more difficult to handle, in contrast to the mentioned non-biological materials, human or animal hard tissues of the same type usually are differing from one individual to the other. Furthermore, human or animal hard tissues usually are not homogeneous such that the photoablation properties of the tissue can vary within one single tissue target particularly depending on the cutting depth. For preventing such excess or unwanted photoablation, depth of the photoablation in the tissue is usually optically monitored, e.g., by means of optical coherence tomography (OCT). However, such monitoring usually is rather complicated and cumbersome. If used in laser ablation such optical monitoring of the depth slows down the cutting or operation of the laser.

Therefore, there is a need for a method and device allowing convenient ablation of human or animal hard tissue particularly in terms of collateral damages caused to the tissue by a laser beam.

DISCLOSURE OF THE INVENTION

According to the invention this need is settled by a laser ablating device as it is defined by the features of independent claim 1, by a method of manufacturing a laser ablating device as it is defined by the features of independent claim 15, and by a method of operating a laser ablating device as it is defined by the features of independent claim 22. Preferred embodiments are subject of the dependent claims.

In particular, the invention deals with a laser ablating device for cutting human or animal natural or artificial hard tissue. The laser ablating device comprises a cutting laser source, an imaging laser source, a beam mixing structure and a scanner mirror. The cutting laser source is adapted to provide a pulsed cutting laser beam lasing at a wavelength suitable for ablating the hard tissue. The imaging laser source is adapted to provide an imaging laser beam covering a broadband spectral region. The scanner mirror is movable and positioned after the beam mixing structure. The beam mixing structure is adapted to redirect the cutting laser beam of the cutting laser source and/or the imaging laser beam of the imaging laser source such that an optical axis of the cutting laser beam is parallel to an optical axis of the imaging laser beam. The scanner mirror is arranged to direct the imaging laser beam and the cutting laser beam when having parallel optical axes preferably onto a target to be hit by the imaging laser beam and the cutting laser beam.

The term "laser device" generally relates to a device which is arranged to generate a laser beam or which emits light through a process of optical amplification based on the stimulated emission of electromagnetic radiation. Laser is an acronym for "light amplification by stimulated emission of radiation". A laser may differ from other sources of light in that it emits light coherently. Such spatial coherence can allow a laser to be focused to a tight spot, which makes applications such as cutting or lithography possible. The laser ablating device can particularly be a laser osteotome.

The term "laser pulse" as used herein can relate to a comparably short-time laser beam preferably of a given wavelength having a specific temporal width, shape and/or power.

The term "hard tissue" in connection with the substrate to be cut by the laser ablating device can relate to nail tissue, cartilage and particularly to bone tissue. Thus, the laser ablating device can particularly be designed for cutting bones. For being suitable to ablate hard tissue and particularly bone tissue the cutting laser beam can have a wavelength appropriate to evaporate water, i.e. about 2'940 nanometer (nm). The term "artificial" in this connection can relate to a synthetic material for substituting or replacing natural hard tissue. Thus, the term "artificial hard tissue" can refer to synthetically generated tissue or materials used as bone substitutes.

The term "broadband spectral region" can relate to a range of light or of electromagnetic waves being broad enough for providing data sufficient or of sufficient quality to evaluate and derive appropriate information about the ablation. For example broadband spectral region can relate to a spectrum of electromagnetic wavelength of about 50 nm, in particular covering a spectral width of 10 nm to 100 nm, in particular of 20 nm to 90 nm, in particular of 30 nm to 80 nm, in particular of 40 nm to 70 nm or in particular of 45 nm to 60 nm.

The term "movable" in connection with the scanner mirror relates to the mirror being displaceable and/or particularly re-orientable. For example, the scanner mirror can be rotated, relocated, tilted, bent or the like in order to be movable. Such movable scanner mirror allows for precisely directing and/or focusing the laser beams or composite laser beam.

The term "positioned after the beam mixing structure" in connection with the movable scanner mirror particularly relates to an arrangement or positioning with respect to a direction of laser beam propagation. In particular, the mirror is positioned such that the laser beams first pass the beam mixing structure and thereafter reach the scanner mirror. Like this, it can be achieved that the mixed laser beams or the composite laser beam is redirected by the scanner mirror. By being positioned after the beam mixing structure, the movable scanner mirror can be positioned behind the beam mixing structure in a laser beam propagation direction.

The term "parallel" in connection with the optical axis of the cutting and the imaging laser beams can relate to a geometrical parallel arrangement, to an orientation essentially parallel, i.e. including minor deviations in alignment, and particularly to an essentially or precisely coaxial orientation of the laser beams.

By the scanner mirror directing the imaging laser beam and the cutting laser beam with parallel optical axes the cutting and imaging laser beams are propagated in the same direction such that they strike the hard tissue or target in the same region or on the same spot. This allows for gathering information via the imaging laser beam of more or less precisely the same location or area where the cutting laser beam hits and ablates the hard tissue. Said information can comparably closely relate to the effect of the cutting laser beam such that efficient, fast and precise conclusions can be drawn in order to minimize or prevent collateral damages caused to the hard tissue by the cutting laser beam.

Furthermore, by combining the laser beams, precisely directing the composite laser beam can be performed or realized by the same components. This allows for a comparably efficient and simple implementation.

Due to the parallel or coaxial orientation of the optical axes, blurring effects caused by a temporal and/or spatial deviation between different laser beams hitting the hard tissue can be reduced or eliminated. This allows for efficiently providing an accurate feedback on the conditions of the hard tissue ablated by the cutting laser beam. Like this, the evaluation can be comparably quick such as real-time.

The term "coaxial" in this connection relates to a spatial relation between the propagating axes of different light beams. It has no meaning regarding temporal relations which may arise by having multiple pulsed laser beams.

The term "real-time" in this connection can relate to an operation of the laser device in which the pulsed cutting laser beam is provided without any restrictions and the cutting evaluation and planning is performed in between the single pulses of the cutting laser beam. A delay in operation of the cutting laser beam is prevented.

In particular, the controlling unit preferably is arranged and configured to evaluate a reflection of the imaging laser beam in real-time.

Also, the evaluation of the parallel laser beams can efficiently be implemented to adapt the laser for automatic reactions on the gathered information. Thus, the laser ablating device allows for a convenient ablation of the hard tissue.

Preferably, the beam mixing structure is an optomechanical structure. Such an optomechanical structure can comprise beam shaping optics to collimate each individual laser beam, deflection mirrors in the different beam paths to allow proper parallel alignment of the laser beams and/or dichroic mirrors to combine the parallel laser beams. In some embodiments, it can be favorable to have the imaging laser beam in transmission for the beam mixing structure. To protect optical elements from impurity the beam mixing structure can comprise an out-coupling window that follows the scanner mirror.

For focusing the composite laser beam the laser ablation device can be equipped with a beam-focusing element which can be comprised by the scanner mirror. The beam-focusing element can be a lens system, reflective optics or a combination of both. Preferably, the scanner mirror as reflective optics is adapted to focus the cutting laser beam and the imaging laser beam. Thereby, the scanner mirror can be a concave mirror mounted on a movable scanning unit which can simplify alignment and controlling. Such a reflective optics design has further the advantage of smaller losses and no chromatic aberrations when using different wavelengths. In this way, a particular efficient operation of the laser ablating device is possible.

Preferably, the laser ablating device further comprises a controlling unit being arranged and configured to evaluate a reflection of the imaging laser beam between two subsequent cutting laser pulses of the cutting laser beam.

The term "arranged and configured to" in connection with the controlling unit can relate to the control system being embodied to be capable of performing certain functions. Thereby, the controlling unit can be equipped and provided with the necessary structure such as connections to a power supply, a central processing unit (CPU), a memory and the like (arranged). Furthermore, it or its structure can be adjusted, adapted or programmed to perform the necessary functions (configured).

The controlling unit can be implemented in any manner suitable for achieving its function or purpose. Advantageously, it is an embedded system integrated in the electronics of the laser sources. For example, it can be integrated, e.g. as a specific circuit, on the circuit board controlling the laser beams. Like this, a particular fast evaluation of the reflection is possible and the laser beams can quickly be adapted in response to this evaluation.

The processing unit can comprise several interfaces to internal and external components such as a nozzle, a temperature camera, the laser sources and the like. Advantageously, it has an external user interface to define cutting geometries, set parameters and visualize progress and system status. The laser ablation device may be combined with additional actuators to increase working range and tracking devices to follow movement of working range and/or actuators. This may require additional interfaces in the controlling unit to these devices.

For example, to ensure proper hardware controlling the controlling unit can comprise the following interfaces to internal devices: analog and digital inputs/outputs (I/Os) for the imaging laser source including analog measurement signals; analog and digital I/Os for the cutting laser source; analog and digital I/Os for the optomechanics of the beam mixing structure; communication means to the temperature camera; an interface to the cooling unit or nozzle to ensure carbonization free cutting; on/off of an aiming laser source.

The controlling unit allows for automatically evaluating the information gathered by the imaging laser source. Thereby, it can evaluate the reflection of the imaging laser beam in terms of its physical properties such as intensity, wave length, phase and/or the like. As a result of this evaluation the control unit can automatically take any measures such as initiating changes of the cutting laser beam.

Thereby, the controlling unit preferably is arranged and configured to evaluate the reflection of the imaging laser beam from the surface being ablated immediately before and immediately after each cutting laser pulse of the cutting laser beam.

The term "immediately" in this connection can relate to as temporally close to the laser pulse as technically or reasonably feasible. In particular, it can relate to respective evaluations as short as possible or appropriate before the laser pulse and as short as possible or appropriate after the laser pulse. Like this, information about the spot of the hard tissue at a spot where it is hit by the cutting laser beam can be obtained before and after the laser pulse. This allows for adjusting the cutting laser beam before being provided and to know about the result of the laser pulse. For example, when the ablating laser is operated at 10 Hz, a reasonable time difference is in the order of milliseconds. For other pulse frequencies other time differences may be appropriate.

Preferably, the controlling unit is arranged and configured to control the cutting laser beam according to information derived from the evaluated reflection of the imaging laser beam. Like this, the cutting laser beam can automatically be adjusted.

Thereby, controlling the cutting laser beam preferably comprises changing the power of a next cutting laser beam pulse. For example, if the information derived from the evaluated reflection of the imaging laser beam shows that the bone structure still is comparably thick or the ablation depth is less than expected the power of the next cutting laser beam pulse can be automatically raised.

Additionally or alternatively, the cutting laser beam preferably comprises changing the repetition rate of the cutting laser beam pulses of the cutting laser beam.

Further additionally or alternatively, controlling the cutting laser beam preferably comprises changing a shape of a next cutting laser beam pulse. The term "shape" in connection with the cutting laser beam pulses" can relate to properties of the laser beam pulses such as their temporal width, height or intensity. For example, it can relate to their form in connection with time vs. intensity or the like.

The information derived from the evaluated reflection of the imaging laser beam preferably comprises a transversal cross section of a cut in the bone. The term "transversal" can particularly relate to a cross section not being in the direction of the cut. Thereby, the cut can be predefined, e.g. in a preoperative planning step, by setting an osteotomic line or osteotomic geometry. The transversal cross section can be a cross section perpendicular to the direction of the cut or osteotomic line. It can also be a cross section deviating from the perpendicular orientation such as an angular or a quasi diagonal orientation.

With such transversal cross section the laser ablating device can involve image processing which allows extracting a reliable depth value out of the processed transversal cross section of the cut (B-Scan) in the bone. This can be performed as follows: The reconstructed B-Scan is first filtered transverse to the A-Scan direction (z-direction). In particular, a median filter can be applied. This has the effect to significantly attenuate noise which is varying between A-Scans. However, the bone surface signal remains strong, inasmuch as the bone surface tends to be similar to the filter direction. In a second step, a depth histogram is computed. In each A-Scan, the maximum intensity is localized and its corresponding single depth value is stored. The assumption is that the origin of the maximum signal intensity is the bone surface. Based on the single depth values of all A-Scans in the B-Scan, a histogram is computed. The depth histogram reflects the distribution of the measured depths within a B-Scan. Ideally, there are two peaks: One for the bone surface and a second for the cut surface. Certainly, reality looks different, in as much as there are many more peaks. To tackle this problem, weak peaks are excluded as candidates. From the remaining peaks, the first and last peak are considered as bone surface and cut surface, whereas the exact assignment does not matter. The final cutting depth value is the depth difference between these two identified peaks.

The A-Scan can be defined as a one dimensional element with a fixed number of points (vector) acquired with an OCT-System at a single point on the working area. Such an A-Scan comprehends a single depth profile. Combining multiple A-Scans by moving the focal point on the working area in a certain path, a two dimensional image called B-Scan can be create. Preferably such a B-Scan is a transversal scan over a cut region resulting in a cross sectional depth profile of the cut.

Alternatively or additionally, the information derived from the evaluated reflection of the imaging laser beam preferably comprises an indication of a distance to tissue neighboring the hard tissue in direction of ablation (z-direction). Such an indication can be the amount of light or the polarization of the light reflected from a neighboring tissue which allows for interpolating the distance to the neighboring tissue. For example, when cutting bone the underlining tissue will be visible as a reflection after the bone reached less than about 0.5 mm or less. Thus, it can be evaluated how far away the neighboring tissue is and the ablation can be stopped exactly when the hard tissue is cut through or closely beforehand. Or the cutting laser beam can be adjusted, e.g. its power lowered, the deeper the cut is and the closer the neighboring tissue gets.

Preferably, the imaging laser source is comprised by an OCT system. In this connection the abbreviation OCT relates to optical coherence tomography particularly being an established medical imaging technique that uses light to capture micrometer-resolution, three-dimensional images from within optical scattering media such as the hard tissue. Thereby, the complete OCT system can be comprised by the laser ablating device. Such OCT system can have a broad band swept source, fiber optics, including a transmission reference arm and connection to beam shaping optics and a balanced detection unit. The output signal can be digitized by the processing unit and the resulting raw signal can undergo a dedicated signal processing before the depth value is extracted by means of imaging processing. The core steps of the signal processing can be DC removal, Fourier Transformation (frequency to spatial domain), dispersion compensation and depending on the acquisition mode a remapping function in the frequency domain. Such OCT system allow for precisely and quickly receiving information about the geometry of the ablation and particularly of the depth of the ablation.

Thereby, the imaging laser beam preferably is wavelength scanable. Such an imaging laser beam allows for an efficient evaluation and for efficiently gathering information about the hard tissue. Alternatively or additionally, the imaging laser beam is a fixed broadband wavelength emission.

Preferably, a temporal pulse width of the cutting laser beam is in a range of about 1 nanosecond to about 1 millisecond or in a range of about 1 microsecond to about 900 microseconds or in a range of about 200 microseconds to about 500 microseconds. Such temporal width can allow for efficiently cutting human or animal hard tissue without allowing the temperature to be elevated to a harming level during one single laser pulse.

Preferably, a pause between two subsequent cutting laser beam pulses is in a range of about 1 millisecond to about 200 milliseconds or in a range of about 10 milliseconds to about 100 milliseconds.

Preferably, the laser ablating device comprises a temperature sensor arranged to sense a temperature of a surface of the hard tissue after being hit by a cutting beam laser pulse generated by the cutting laser source. In particular, the temperature sensor can be arranged to sense a temperature of a surface of the target immediately after or while being hit by the cutting beam laser pulse. Such a temperature sensor allows for real-time monitoring the temperature at the target site. In particular, when the target is a temperature sensitive material such as a human or animal hard tissue that can be degraded or destroyed during the ablation process monitoring the temperature becomes very important. For example, when cutting a human or animal hard tissue it is important to prevent the temperature of the tissue to exceed a threshold. Otherwise, the large amount of heat transferred to locations of the cut line or cut geometry and the remaining tissue carbonizes the surfaces precluding or delaying subsequent healing. Thus, controlling the temperature is essential in medical applications.

Thereby, the temperature sensor preferably comprises a remote infrared sensor. In this context, the term "remote" relates to a position of the sensor with respect to the target or material to be treated by the laser. In particular, the sensor can be remote by being offset or distant from the target without contacting it. For example, such sensor allows for being arranged at the laser and no contact to the target is necessary for monitoring the temperature while laser pulses are provided to the target. Thus, such remote infrared sensor preferably with and appropriate imaging optics allows for efficiently and precisely monitoring the temperature of the target when being treated by the laser.

Preferably, the laser ablating device further comprises an aiming laser source adapted to provide a visible aiming laser beam for indicating a target location where the cutting laser beam is intended to impact the hard tissue. Therein, the beam mixing structure is adapted to redirect the aiming laser beam of the aiming laser source such that an optical axis of the aiming laser beam is parallel to the optical axis of the imaging laser beam and to the optical axis of the cutting laser beam, and the scanner mirror is arranged to direct the aiming laser beam, the imaging laser beam and the cutting laser beam when having parallel optical axes.

The aiming laser beam can particularly be an aiming laser beam as it is defined in regulatory provisions. Such definition can be: Beam of optical radiation, producing a visible aiming beam spot intended for indication of the anticipated point of impact of a working beam, i.e. the cutting laser beam. The aiming beam spot can be defined as an area of impact of the aiming laser beam within the working area, i.e. the hard tissue. The aiming laser can be defined as laser emitting the aiming laser beam.

A further aspect of the present invention relates to a method of manufacturing a laser ablating device for cutting human or animal natural or artificial hard tissue (manufacturing method). The manufacturing method comprises assembling the laser ablating device with a cutting laser source adapted to provide a pulsed cutting laser beam lasing at a wavelength suitable for ablating the hard tissue, and an imaging laser source adapted to provide an imaging laser beam covering a broadband spectral region. It further comprises the steps of: assembling the laser ablating device with a beam mixing structure and a movable scanner mirror positioned after the beam mixing structure, adapting the beam mixing structure to redirect the cutting laser beam of the cutting laser source and/or the imaging laser beam of the imaging laser source such that an optical axis of the cutting laser beam is parallel to an optical axis of the imaging laser beam, and arranging the scanner mirror to direct the imaging laser beam and the cutting laser beam when having parallel optical axes.

Such a manufacturing method allows for efficiently providing the laser ablating device according to the invention as well as its effects and benefits. The manufacturing method can further comprise steps or be arranged for implementing the additional features of the preferred embodiments of the laser ablating device described above. In this way the effects and advantages mentioned above in connection with the respective additional features can efficiently be implemented.

Preferably, the manufacturing method further comprises: assembling the laser ablating device with a controlling unit; and arranging and configuring the controlling unit to evaluate a reflection of the imaging laser beam between two subsequent cutting laser pulses of the cutting laser beam.

Thereby, the manufacturing method preferably comprises arranging and configuring the controlling unit to evaluate the reflection of the imaging laser beam between two subsequent cutting laser pulses of the cutting laser beam in real-time.

Also, the manufacturing method preferably comprises arranging and configuring the controlling unit to evaluate the reflection of the imaging laser beam immediately before and immediately after each cutting laser pulse of the cutting laser beam.

Preferably, the manufacturing method comprises arranging and configuring the controlling unit to control the cutting laser beam according to information derived from the evaluated reflection of the imaging laser beam. Thereby, controlling the cutting laser beam preferably comprises changing the power of a next cutting laser beam pulse. Additionally or alternatively, controlling the cutting laser beam preferably comprises changing the repetition rate of the cutting laser beam pulses of the cutting laser beam. Further additionally or alternatively, controlling the cutting laser beam preferably comprises changing a shape of a next cutting laser beam pulse.

The information derived from the evaluated reflection of the imaging laser beam preferably comprises a transversal cross section of a cut in the bone. Alternatively or additionally, the information derived from the evaluated reflection of the imaging laser beam preferably comprises an indication of a distance to tissue neighboring the hard tissue.

Another further aspect of the invention relates to a method of cutting human or animal natural or artificial hard tissue (cutting method). The cutting method comprises the steps of: a cutting laser source providing a pulsed cutting laser beam lasing at a wavelength suitable for ablating the hard tissue; an imaging laser source providing an imaging laser beam covering a broadband spectral region; a beam mixing structure redirecting the cutting laser beam of the cutting laser source and/or the imaging laser beam of the imaging laser source such that an optical axis of the cutting laser beam is parallel to an optical axis of the imaging laser beam; and a movable scanner mirror positioned after the beam mixing structure directing the imaging laser beam and the cutting laser beam when having parallel optical axes. The same cutting method can also be applied for cutting targets other than human or animal natural or artificial hard tissues.

Such a cutting method allows for efficiently achieving the effects and benefits described above in connection with the laser ablating device according to the invention. The cutting method can further comprise steps or be arranged for implementing the additional features of the preferred embodiments of the laser ablating device described above. In this way the effects and advantages mentioned above in connection with the respective additional features or preferred embodiments can efficiently be implemented.

Preferably, the cutting method further comprises a controlling unit evaluating a reflection of the imaging laser beam between two subsequent cutting laser pulses of the cutting laser beam. Thereby, the controlling unit preferably evaluates the reflection of the imaging laser beam between two subsequent cutting laser pulses of the cutting laser beam in real-time.

Preferably, the cutting method comprises the controlling unit evaluating the reflection of the imaging laser beam immediately before and immediately after each cutting laser pulse of the cutting laser beam.

Preferably, the cutting method comprises the controlling unit controlling the cutting laser beam according to information derived from the evaluated reflection of the imaging laser beam.

Thereby, controlling the cutting laser beam preferably comprises changing the power of a next cutting laser beam pulse. Additionally or alternatively, controlling the cutting laser beam preferably comprises changing the repetition rate of the cutting laser beam pulses of the cutting laser beam. Further, alternatively or additionally controlling the cutting laser beam preferably comprises changing a shape of a next cutting laser beam pulse.

The information derived from the evaluated reflection of the imaging laser beam preferably comprises a transversal cross section of a cut in the bone, preferably comprising depth information of such a cut. Additionally or alternatively, the information derived from the evaluated reflection of the imaging laser beam preferably comprises an indication of a distance to tissue neighboring the hard tissue.

Preferably, the cutting method is not a method for treatment of the human or animal body by surgery or therapy, nor a diagnostic method practiced on the human or animal body.

Still another further aspect of the invention relates to a method of operating a laser ablating device (operating method). The operating method comprises the steps of: a cutting laser source of the laser ablating device providing a pulsed cutting laser beam preferably lasing at a wavelength suitable for ablating a human or animal natural or artificial hard tissue; an imaging laser source of the laser ablating device providing an imaging laser beam covering a broadband spectral region; a beam mixing structure of the laser ablating device redirect the cutting laser beam of the cutting laser source and/or the imaging laser beam of the imaging laser source such that an optical axis of the cutting laser beam is parallel to an optical axis of the imaging laser beam; and a movable scanner mirror of the laser ablating device positioned after the beam mixing structure of the laser ablating device directing the imaging laser beam and the cutting laser beam having parallel optical axes.

Such an operating method allows for efficiently achieving the effects and benefits described above in connection with the laser ablating device according to the invention. The operating method can further comprise steps or be arranged for implementing the additional features of the preferred embodiments of the laser ablating device described above. In this way the effects and advantages mentioned above in connection with the respective additional features or preferred embodiments can efficiently be implemented.

Preferably, the operating method comprises the scanner mirror of the laser ablating device focusing the cutting laser beam and the imaging laser beam.

Preferably, the operating method comprises a controlling unit of the laser ablating device evaluating a reflection of the imaging laser beam between two subsequent cutting laser pulses of the cutting laser beam.

Thereby, the controlling unit of the laser ablating device preferably evaluates the reflection of the imaging laser beam between two subsequent cutting laser pulses of the cutting laser beam in real-time.

Also, the operating method preferably comprises the controlling unit evaluating the reflection of the imaging laser beam immediately before and immediately after each cutting laser pulse of the cutting laser beam.

Preferably, the operating method comprises the controlling unit of the laser ablating device controlling the cutting laser beam according to information derived from the evaluated reflection of the imaging laser beam. Thereby, the controlling unit of the laser ablating device controlling the cutting laser beam preferably comprises changing the power of a next cutting laser beam pulse.

The information derived from the evaluated reflection of the imaging laser beam preferably comprises an indication of a distance to tissue neighboring the hard tissue.

Preferably, the controlling unit of the laser ablating device controlling the cutting laser beam comprises changing the repetition rate of the cutting laser beam pulses of the cutting laser beam. Alternatively or additionally, the controlling unit of the laser ablating device controlling the cutting laser beam preferably comprises changing a shape of a next cutting laser beam pulse.

Preferably, the information derived from the evaluated reflection of the imaging laser beam comprises a transversal cross section of a cut in the bone.

Preferably, the cutting laser source of the laser ablating device provides the cutting laser beam with a temporal pulse width in range of about 1 nanosecond to about 1 millisecond or in arrange of about 1 microsecond to about 900 microseconds or in range of about 100 microseconds to about 700 microseconds.

The cutting laser source of the laser ablating device preferably provides the cutting laser beam with a pause between two subsequent cutting laser beam pulses being a range of about 1 millisecond to about 200 milliseconds or in a range of about 10 milliseconds to about 100 milliseconds.

Preferably, the operating method comprises a temperature sensor of the laser ablating device sensing a temperature of a surface of the hard tissue after being hit by a cutting beam laser pulse generated by the cutting laser source of the laser ablating device.

Preferably, operating method further comprises the step of: an aiming laser source of the laser ablating device providing a visible aiming laser beam for indicating a target location where the cutting laser beam is intended to impact the hard tissue, wherein the beam mixing structure of the laser ablating device redirects the aiming laser beam of the aiming laser source of the laser ablating device such that an optical axis of the aiming laser beam is parallel to the optical axis of the imaging laser beam and to the optical axis of the cutting laser beam, and the scanner mirror of the laser ablating device directs the aiming laser beam, the imaging laser beam and the cutting laser beam when having parallel optical axes.

BRIEF DESCRIPTION OF THE DRAWINGS

The laser ablating device and methods according to the invention are described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the nozzle device in use or operation in addition to the position and orientation shown in the figures. For example, if the device or a specific part thereof in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description.

In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
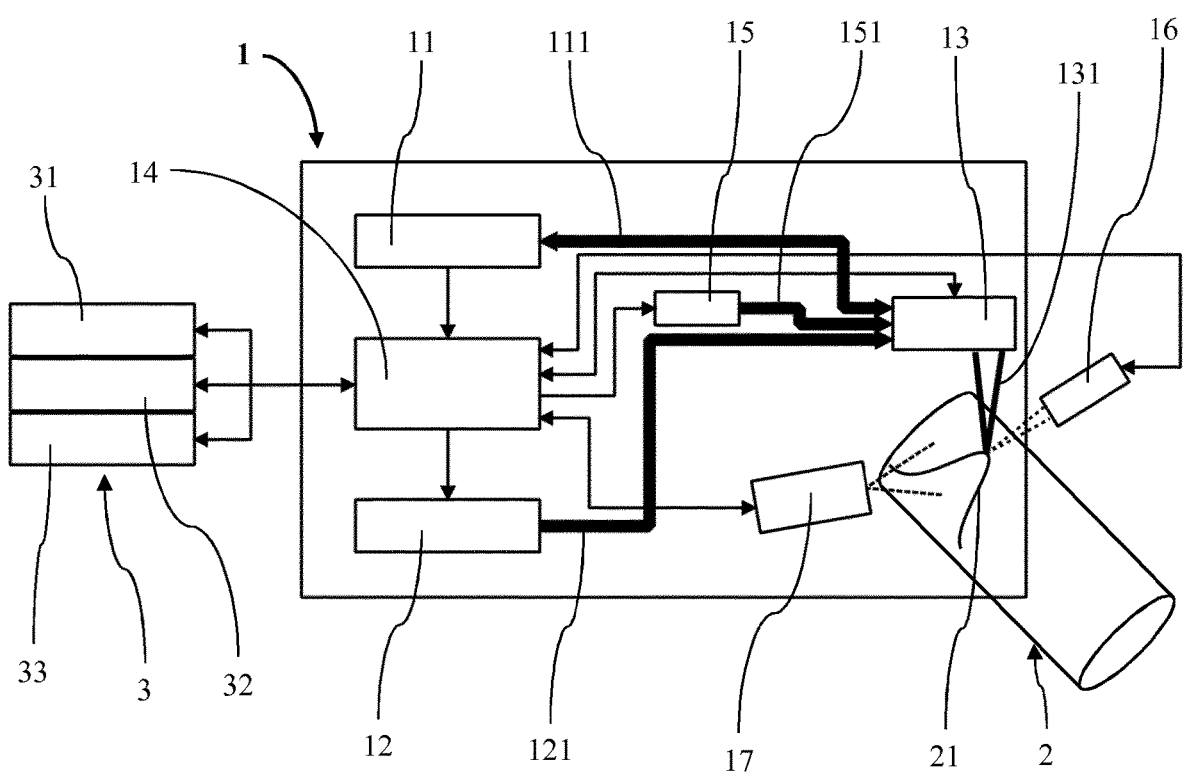
FIG. 1 shows a setup of an embodiment of a laser ablating device according to the invention.

FIG. 1 shows a schematic illustration of an embodiment of a laser ablating device 1 according to the invention. The laser ablating device 1 comprises an OCT laser source 11 as imaging laser source, a cutting laser source 12, an aiming laser source 15 and a controlling unit 14. The OCT laser source 11 is arranged to provide an imaging laser beam 111 covering a broadband spectral region of 50 nm. The cutting laser source 12 is arranged to provide a pulsed cutting laser beam 121 which is capable of ablating tissue of a bone 2. The aiming laser source 15 is arranged to provide an aiming laser beam 151 of visible light.

The laser ablating device 1 further comprises a beam configurator 13 which is arranged to collect the imaging laser beam 111, the cutting laser beam 121 and the aiming laser beam 151 and to combine them to a composite laser beam 131. The composite laser beam 131 is provided to the bone 2. In particular, it is driven along an osteotomic line 21 preoperatively defined on the bone 2 or on an image thereof. For driving the composite laser beam 131 along the osteotomic line 21, on one hand the beam configurator 13 has respective guiding means as explained in more detail below in connection with FIG. 2. On the other hand the laser ablating device 1 is mounted to a robotic arm 31 of an actuating support system 3 which allows for precisely moving the laser ablating device 1 to a greater extent than possible by the guiding means of the beam configurator 13.

The actuating support system 3 further comprises a navigator 32 and a user interface 33. The user interface 33 is arranged to allow a user or operator to interact with the controlling unit 14 of the laser ablating device 1.

The controlling unit 14 comprises a number of interfaces for communicating with other components within or outside the laser ablation device 1. In particular, via these interfaces it is connected to the robotic arm 31, the navigator 32, the user interface 33, the cutting laser source 12, the OCT laser source 11, the aiming laser source 15, the beam configurator 13, a cooling nozzle 16 and an infrared (IR) camera 17 as temperature sensor.

The controlling unit 14 is adapted or arranged and configured to perform a plurality of tasks when operating the laser ablating device 1. It evaluates the reflection of the imaging laser beam 111 between two subsequent pulses of the cutting laser beam 121 and as can be seen in more detail in in FIG. 4 below immediately after each pulse of the cutting laser beam 121. By evaluating this reflection the controlling unit 14 derives information about the effect of the pulse of the cutting laser beam 121 such as a transversal cross section of the ablated tissue. Depending on this information the controlling unit adjusts cutting laser source 12 such that the next pulse of cutting laser bream 121 fits to the actual situation at the tissue. Such adjustment may comprise changing the power of the cutting laser beam 121, changing its repetition rate, changing its beam shape and the like.

The cooling nozzle 16 is adapted to spray a cooling medium towards the bone 2 at a spot where the composite laser beam 131 hits the tissue of the bone 2, i.e. at the osteotomic line 21. The cooling medium can particularly be a preferably sterile liquid such as water combined with a gas such as air. Thereby, cooling can be adjusted by the controlling unit 14 by adjusting the composition, the conditions and the direction of the spray generated by the nozzle 16.

The IR camera 17 is also directed towards the bone 2 at a spot where the composite laser beam 131 hits the tissue of the bone 2, i.e. at the osteotomic line 21. Thereby, it constantly measures the temperature of the tissue while being ablated. In case the temperature exceeds a specific threshold such as, e.g., 45° C. the controlling unit 14 interrupts the provision of the cutting laser beam 121 until the tissue is sufficiently cooled again.

Figure 2:
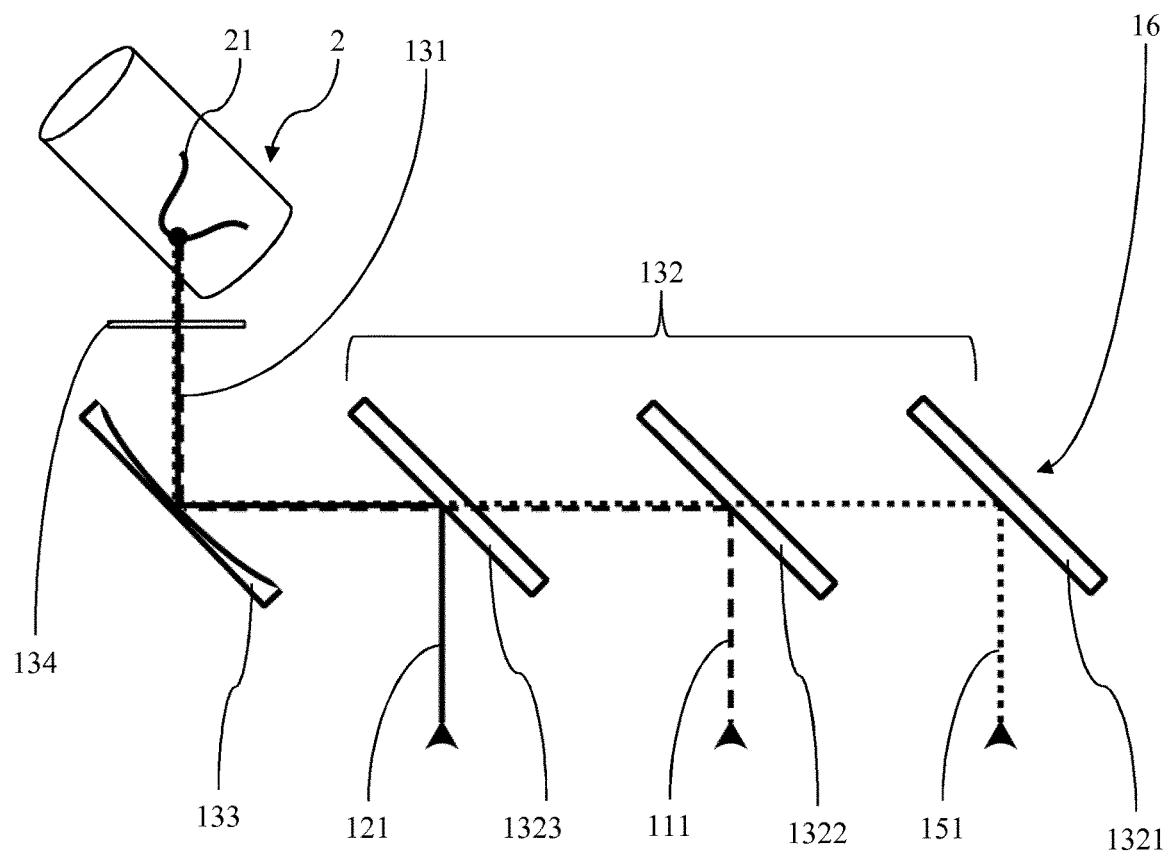
FIG. 2 shows details of a beam configurator of the laser ablating device of FIG. 1.

In FIG. 2 the beam configurator 13 of the laser ablating device 1 is shown in more detail. It is equipped with a parabolic mirror 133 as scanner mirror and an optomechanical system 132 as beam mixing structure comprising a mirror 1321, a first dichroic mirror 1322 and a second dichroic mirror 1323. The mirror 1321 is arranged to redirect the aiming laser beam 151 to the back side of the first dichroic mirror 1322. The first dichroic mirror 1322 is transparent for the aiming laser beam 151 and redirects the imaging laser beam 111 into the same direction as the aiming laser beam 151 towards the back side of the second dichroic mirror 1323. The second dichroic mirror 1323 is transparent for the aiming laser beam 151 and the imaging laser beam 111. It redirects the cutting laser beam 121 into the same direction as the aiming laser beam 151 and the imaging laser beam 111 towards the parabolic mirror 133.

At this stage the optical axes of the aiming laser beam 151, the imaging laser beam 111 and the cutting laser beam 121 are parallel or coaxial such that together they form the composite laser beam 131. The parabolic mirror 133 is movable and adjustable by the controlling unit 14. Like this, it focusses and directs the composite laser beam 131 via an out-coupling window 134 precisely along the osteotomic line 21 to the bone 2. Thus, it establishes the guiding means of the beam configurator 13.

Figure 3:
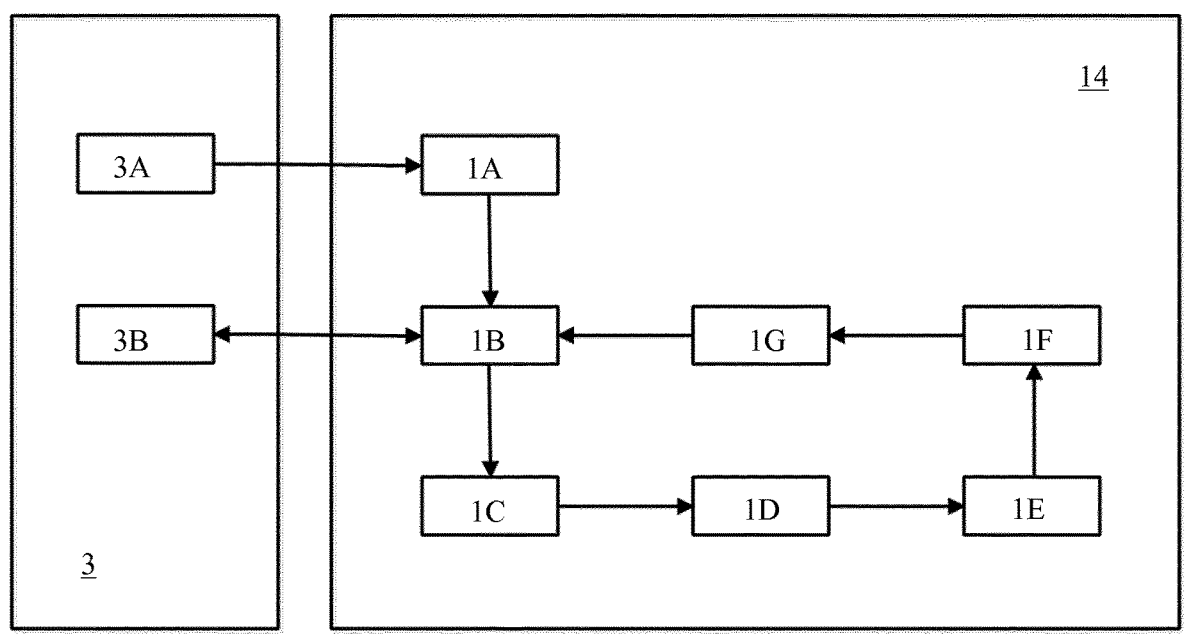
FIG. 3 shows a course of an embodiment of operating and cutting methods according to the invention.

FIG. 3 shows a workflow of operation of the laser ablating device 1. Start is the setup of the cutting execution and their parameters which requires a user input from the external higher level system 3A such as via the user interface 33. In a second step the cutting design is loaded to the controlling unit 14 from external 1A and the controlling unit 14 plans the first cutting laser pulse 1B which is followed by defining the cutting parameters 1C. Prior the first cutting laser beam pulse the controlling unit 14 sets the beam configurator 13 according the planned position 1D. Then the laser ablation is executed by providing a pulse of the cutting laser beam 121 pulse 1E. Depending on configuration the imaging laser beam 111 measurement is acquired 1F before and/or after the cutting laser beam pulse 1E. Directly after the acquisition this reflection is evaluated by the controlling unit 14 1G and the cutting execution is updated by planning the next cutting laser beam pulse 11B. Depending on the use of external actuators and/or tracking systems this step requires interaction with external components 3B or not.

Figure 4:
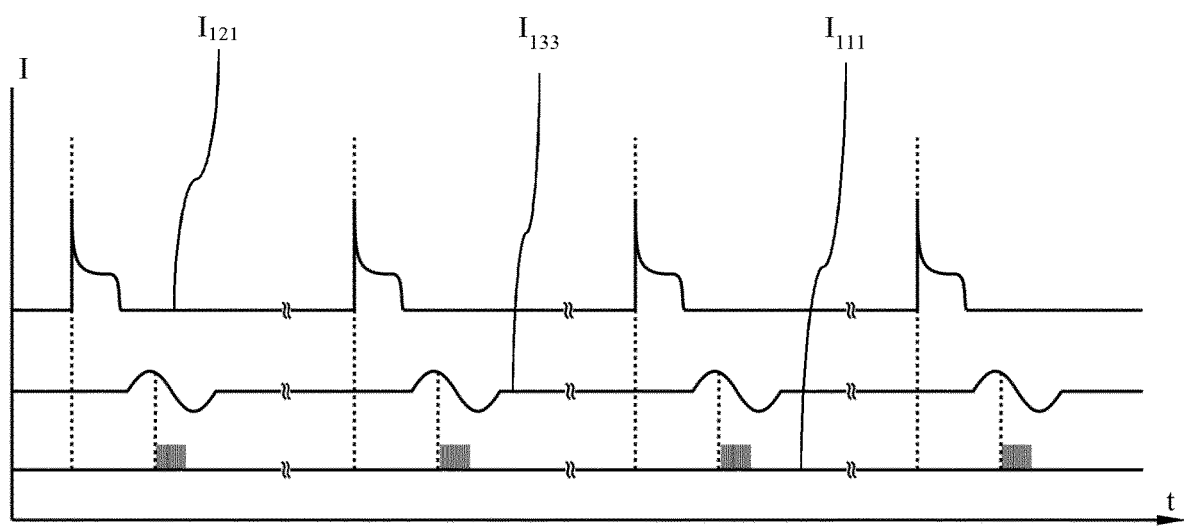
FIG. 4 shows operation of the laser ablating device of FIG. 1 in the method of FIG. 3.

In FIG. 4 graphs of indexes $I_{121}$, $I_{133}$, $I_{111}$ representing actions of the cutting laser source 12, the parabolic mirror 133 and the OCT laser source 111 are shown. Thereby, it can be seen that immediately after a cutting laser beam 121 pulse is provided (represented by index $I_{121}$) the parabolic mirror 133 is moved (represented by index $I_{133}$) such that the location of the bone 2 where tissue is ablated is scanned. Thereby, the OCT laser beam 111 which is constantly provided allows for generating a cross sectional image of the cut of the bone 2 (represented by index $I_{111}$). From this image at least the depth is derived by the controlling unit 14 and conclusions are drawn for adapting the next cutting laser beam 121 pulse if appropriate.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A laser ablating device for cutting human or animal natural or artificial hard tissue, comprising:
   a cutting laser source adapted to provide a pulsed cutting laser beam lasing at a wavelength suitable for ablating the hard tissue;
   an imaging laser source adapted to provide an imaging laser beam covering a broadband spectral region;
   a beam mixing structure;
   a movable scanner mirror positioned after the beam mixing structure; and
   a controlling unit,
   wherein
   the beam mixing structure is adapted to redirect the cutting laser beam of the cutting laser source and/or the imaging laser beam of the imaging laser source such that an optical axis of the cutting laser beam is parallel to an optical axis of the imaging laser beam,
   the scanner mirror is arranged to direct the imaging laser beam and the cutting laser beam when having parallel optical axes,
   the controlling unit is arranged and configured to evaluate a reflection of the imaging laser beam between two subsequent cutting laser pulses of the cutting laser beam,
   the controlling unit is arranged and configured to evaluate a reflection of the imaging laser beam in real-time,
   the controlling unit is arranged and configured to evaluate the reflection of the imaging laser beam immediately before and immediately after each cutting laser pulse of the cutting laser beam resulting in two imaging evaluations between each cutting laser pulse, and
   the controlling unit is arranged and configured to control the cutting laser beam of one cutting laser beam pulse according to information derived from the evaluated reflection of the imaging laser beam provided immediately before and after a cutting laser beam pulse preceding the one cutting laser beam pulse, wherein a temporal pulse width of the cutting laser beam is in a range of about 1 nanosecond to about 1 millisecond or in a range of about 1 microsecond to about 900 microseconds or in a range of about 200 microseconds to about 500 microseconds, and a pause between two subsequent cutting laser beam pulses is in a range of about 1 millisecond to about 200 millisecond or in a range of about 10 milliseconds to about 100 milliseconds.

2. The laser ablating device of claim 1, wherein controlling the cutting laser beam comprises changing a power of a next cutting laser beam pulse, a repetition rate of the cutting laser beam pulses of the cutting laser beam, and/or a shape of a next cutting laser beam pulse.

3. The laser ablating device of claim 1, wherein the information derived from the evaluated reflection of the imaging laser beam comprises a transversal cross section of a cut in the hard tissue and/or an indication of a distance to tissue neighboring the hard tissue.

4. The laser ablating device of claim 1, wherein the imaging laser source is comprised by an OCT system.

5. The laser ablating device of claim 1, comprising a temperature sensor arranged to sense a temperature of a surface of the hard tissue after being hit by a cutting beam laser pulse generated by the cutting laser source.

6. The laser ablating device of claim 5, wherein the temperature sensor comprises a remote infrared sensor.

7. The laser ablating device of claim 1, further comprising an aiming laser source adapted to provide a visible aiming laser beam for indicating a target location where the cutting laser beam is intended to impact the hard tissue, wherein the beam mixing structure is adapted to redirect the aiming laser beam of the aiming laser source such that an optical axis of the aiming laser beam is parallel to the optical axis of the imaging laser beam and to the optical axis of the cutting laser beam, and the scanner mirror is arranged to direct the aiming laser beam, the imaging laser beam and the cutting laser beam when having parallel optical axes.

8. The laser ablating device of claim 1, wherein the beam mixing structure comprises an optomechanical structure, and/or the scanner mirror is adapted to focus the cutting laser beam and the imaging laser beam.

9. The laser ablating device of claim 1, wherein the imaging laser beam is a wavelength scannable laser beam and/or a fixed broadband wavelength emission.

10. A method of operating a laser ablating device, comprising:

a cutting laser source of the laser ablating device providing a pulsed cutting laser beam;

an imaging laser source of the laser ablating device providing an imaging laser beam covering a broadband spectral region;

a beam mixing structure of the laser ablating device redirecting the cutting laser beam of the cutting laser source and/or the imaging laser beam of the imaging laser source such that an optical axis of the cutting laser beam is parallel to an optical axis of the imaging laser beam;

a movable scanner mirror of the laser ablating device positioned after the beam mixing structure of the laser ablating device directing the imaging laser beam and the cutting laser beam having parallel optical axes;

a controlling unit of the laser ablating device evaluating a reflection of the imaging laser beam between two subsequent cutting laser pulses of the cutting laser beam in real-time, and the controlling unit evaluating the reflection of the imaging laser beam immediately before and immediately after each cutting laser pulse of the cutting laser beam resulting in two imaging evaluations between each cutting laser pulse, the controlling unit is arranged and configured to control the cutting laser beam of one cutting laser beam pulse according to information derived from the evaluated reflection of the imaging laser beam provided immediately before and after a cutting laser beam pulse preceding the one cutting laser beam pulse, wherein a temporal pulse width of the cutting laser beam is in a range of about 1 nanosecond to about 1 millisecond or in a range of about 1 microsecond to about 900 microseconds or in a range of about 200 microseconds to about 500 microseconds, and a pause between two subsequent cutting laser beam pulses is in a range of about 1 millisecond to about 200 millisecond or in a range of about 10 milliseconds to about 100 milliseconds.

11. The method of claim 10, comprising the scanner mirror of the laser ablating device focusing the cutting laser beam and the imaging laser beam.

12. The method of claim 10, wherein the cutting laser beam is configured to lase at a wavelength suitable for ablating a human or animal natural or artificial hard tissue.

13. The method of claim 10, comprising the controlling unit of the laser ablating device controlling the cutting laser beam according to information derived from the evaluated reflection of the imaging laser beam, the cutting laser beam comprises changing a repetition rate of the cutting laser beam pulses of the cutting laser beam, and/or the cutting laser beam comprises changing a shape of a next cutting laser beam pulse.

14. The method of claim 13, wherein the information derived from the evaluated reflection of the imaging laser beam comprises a transversal cross section of a cut in hard tissue.

15. The method of claim 13, wherein the controlling unit of the laser ablating device controlling the cutting laser beam comprises changing a power of a next cutting laser beam pulse.

16. The method of claim 13, wherein the information derived from the evaluated reflection of the imaging laser beam comprises an indication of a distance to tissue neighboring hard tissue.

17. The method of claim 10, further comprising a temperature sensor of the laser ablating device sensing a temperature of a surface of hard tissue after being hit by a cutting laser beam pulse generated by the cutting laser source of the laser ablating device, and/or an aiming laser source of the laser ablating device providing a visible aiming laser beam for indicating a target location where the cutting laser beam is intended to impact the hard tissue, wherein the beam mixing structure of the laser ablating device redirects the aiming laser beam of the aiming laser source of the laser ablating device such that an optical axis of the aiming laser beam is parallel to the optical axis of the imaging laser beam and to the optical axis of the cutting laser beam, and the scanner mirror of the laser ablating device directs the aiming laser beam, the imaging laser beam and the cutting laser beam when having parallel optical axes.

18. A method of operating a laser ablating device, comprising:
- a cutting laser source of the laser ablating device providing a pulsed cutting laser beam;
- an imaging laser source of the laser ablating device providing an imaging laser beam covering a broadband spectral region;
- a beam mixing structure of the laser ablating device redirecting the cutting laser beam of the cutting laser source and/or the imaging laser beam of the imaging laser source such that an optical axis of the cutting laser beam is parallel to an optical axis of the imaging laser beam;
- a movable scanner mirror of the laser ablating device positioned after the beam mixing structure of the laser ablating device directing the imaging laser beam and the cutting laser beam having parallel optical axes;
- a controlling unit
- evaluating a reflection of the imaging laser beam between two subsequent cutting laser pulses of the cutting laser beam, wherein the controlling unit evaluates the reflection of the imaging laser beam between two subsequent cutting laser pulses of the cutting laser beam in real-time; and
- evaluating the reflection of the imaging laser beam immediately before and immediately after each cutting laser pulse of the cutting laser beam resulting in two imaging evaluations between each cutting laser pulse,
- controlling the cutting laser beam of one cutting laser beam pulse according to information derived from the evaluated reflection of the imaging laser beam provided immediately before and after a cutting laser beam pulse preceding the one cutting laser beam pulse
- wherein a temporal pulse width of the cutting laser beam is in a range of about 1 nanosecond to about 1 millisecond or in a range of about 1 microsecond to about 900 microseconds or in a range of about 200 microseconds to about 500 microseconds, and
- a pause between two subsequent cutting laser beam pulses is in a range of about 1 millisecond to about 200 millisecond or in a range of about 10 milliseconds to about 100 milliseconds.

19. The method of claim 18, comprising the controlling unit
- controlling the cutting laser beam according to information derived from the evaluated reflection of the imaging laser beam.

20. The method of claim 19, wherein controlling the cutting laser beam comprises
- changing a power of a next cutting laser beam pulse,
- changing a repetition rate of the cutting laser beam pulses of the cutting laser beam, and/or
- changing a shape of a next cutting laser beam pulse.

21. The method of claim 19, wherein the information derived from the evaluated reflection of the imaging laser beam comprises
- a transversal cross section of a cut in hard tissue, and/or
- an indication of a distance to tissue neighboring the hard tissue.

22. The method of claim 18, wherein the pulsed cutting laser beam is configured to lase at a wavelength suitable for ablating a human or animal natural or artificial hard tissue.

* * * * *